US009677134B2

(12) United States Patent
Enoki et al.

(10) Patent No.: US 9,677,134 B2
(45) Date of Patent: Jun. 13, 2017

(54) SUGARCANE-STALK-SUGAR-CONTENT-RELATED MARKER AND THE USE THEREOF

(71) Applicant: TOYOTA JIDOSHA KABUSHIKI KAISHA, Toyota-shi, Aichi (JP)

(72) Inventors: Hiroyuki Enoki, Okazaki (JP); Tatsuro Kimura, Kariya (JP); Shoko Tsuzuki, Nagoya (JP); Satoru Nishimura, Nagoya (JP); Aya Murakami, Toyota (JP); Takayoshi Terauchi, Nishino-omote (JP); Takeo Sakaigaichi, Nishino-omote (JP); Taiichiro Hattori, Nishino-omote (JP); Shoko Ishikawa, Nishino-omote (JP); Yoshifumi Terajima, Ishigaki (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 276 days.

(21) Appl. No.: 14/330,661

(22) Filed: Jul. 14, 2014

(65) Prior Publication Data
US 2014/0349876 A1 Nov. 27, 2014

Related U.S. Application Data

(62) Division of application No. 13/988,711, filed as application No. PCT/JP2011/006685 on Nov. 30, 2011, now abandoned.

(30) Foreign Application Priority Data

Dec. 3, 2010 (JP) ................................. 2010-270769

(51) Int. Cl.
*C12Q 1/68* (2006.01)
*A01H 1/04* (2006.01)
*A01H 5/04* (2006.01)

(52) U.S. Cl.
CPC ............. *C12Q 1/6876* (2013.01); *A01H 1/04* (2013.01); *A01H 5/04* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 8,519,223 | B2 | 8/2013 | Taguchi et al. |
| 2009/0094717 | A1 | 4/2009 | Troukhan et al. |
| 2009/0222941 | A1 | 9/2009 | Taguchi et al. |
| 2011/0154528 | A1 | 6/2011 | Ragot et al. |
| 2015/0052631 | A1 | 2/2015 | Shimada et al. |

FOREIGN PATENT DOCUMENTS

| JP | 2010516236 A | 5/2010 |
| WO | 2007/125958 A1 | 11/2007 |
| WO | 2012/017679 A1 | 2/2012 |

OTHER PUBLICATIONS

Hoarau et al. (Theor. Appl. Genet. (2001) 103: pp. 84-97).*
Office Action issued Apr. 17, 2014, from the United States Patent and Trademark Office in U.S. Appl. No. 13/988,711 in the name of Hiroyuki Enoki.
Office Action issued Feb. 11, 2014, from the United States Patent and Trademark Office in U.S. Appl. No. 13/988,711 in the name of Hiroyuki Enoki.
Office Action issued Nov. 10, 2015, from the United States Patent and Trademark Office in U.S. Appl. No. 14/388,161 in the name of Takehiko Shimada.
Hoarau et al. "Genetic dissection of a modern sugarcane cultivar (*Saccharum* spp.). I. Genome mapping with AFLP markers", Theoretical and Applied Genetics, 2001, vol. 103. pp. 84-97 (2001) (14 pages total).
Pan et al. "Molecular Genotyping of Sugarcane Clones with Microsatellite DNA Markers", Maydica, vol. 48, 2003, pp. 319-329 (2003) (11 pages total).
Ming et al., Genome Research, 11. 12 (2001):2075-2084.
Arruda, P., Accession No. CA124917.1, SCQSLR1061A11.g LR1 Saccharum hybrid cultivar SP80-3280 cDNA clone SCQSLR1061A11 5-, mRNA sequence, Database (online), retrieved from http://www.ncbi.nlm.nih.gov/nucest/CA124917 on Feb. 11, 2014.
Ray Ming, et al., "QTL Analysis in a Complex Autopolyploid Genetic Control of Sugar Content in Sugarcane", Genome Research, Dec. 1, 2001, pp. 2075-2084.
Nathalie Piperidis, et al., "Comparative genetics in sugarcane enables structured map enhancement and validation of marker-trait associations", Mol Breeding, 2008, pp. 233-247, vol. 21,; XP-002662478.
R. Ming, et al., "Molecular dissection of complex traits in autopolyploids: mapping QTLs affecting sugar yield and related traits in sugarcane", Theoretical and Applied Genetics, Aug. 1, 2002, pp. 332-345, vol. 105, No. 2-3.
"SCQSLR1061A11.g LR1 Saccharum hybrid cultivar SP80-3280 cDNA clone SCQSLR1061A11 5', mRNA sequence.", EM_EST:CA124917, Sep. 25, 2003, 1 page.
H. Enoki, et al., "The 117th Meeting of the Japanese Society of Breeding, held in 2010", Mar. 25, 2010, 7 pages.

(Continued)

*Primary Examiner* — Brent Page
*Assistant Examiner* — Jared Shapiro
(74) *Attorney, Agent, or Firm* — Sughrue Mion, PLLC

(57) ABSTRACT

According to the present invention, a sugarcane-stalk-sugar-content-related marker linked to a sugarcane quantitative trait is provided. Such marker is a sugarcane-stalk-sugar-content-related marker, which comprises a continuous nucleic acid region existing in a region sandwiched between the nucleotide sequence shown in SEQ ID NO: 1 and the nucleotide sequence shown in SEQ ID NO: 8 or a region sandwiched between the nucleotide sequence shown in SEQ ID NO: 9 and the nucleotide sequence shown in SEQ ID NO: 16.

2 Claims, 7 Drawing Sheets

(56) References Cited

OTHER PUBLICATIONS

EMBL Accession No. CA124917.1 Sep. 25, 2003, 2 pages total.
GenBank Accession No. CA122736.1 Sep. 23, 2003, 2 pages total.
GenBank Accession No. CA257347.1 Sep. 26, 2003., 2 pages total.
GenBank Accession No. CA137323.1 Sep. 24, 2003., 2 pages total.
Communication, issued Jul. 21, 2016, by the United States Patent and Trademark Office in U.S. Appl. No. 14/388,161.
Communication, dated Jan. 11, 2017, issued by the United States Patent & Trademark Office in U.S. Appl. No. 14/388,161.

\* cited by examiner

```
                         SEQUENCE LISTING

<160> NUMBER OF SEQ ID NOS: 19

<210> SEQ ID NO 1
<211> LENGTH: 50
<212> TYPE: DNA
<213> ORGANISM: Saccharum officinarum

<400> SEQUENCE: 1
ggttcgtcaa ggccaaggcg gcggcgctgg tcggagcgca caaggtgaag             50

<210> SEQ ID NO 2
<211> LENGTH: 75
<212> TYPE: DNA
<213> ORGANISM: Saccharum officinarum

<400> SEQUENCE: 2
atgtatagat gacataagaa aggatgtaat cacttaactg atgcttacta gattattaag  60
caaatataat aggta                                                   75

<210> SEQ ID NO 3
<211> LENGTH: 52
<212> TYPE: DNA
<213> ORGANISM: Saccharum officinarum

<400> SEQUENCE: 3
ttcagcacat tcagcactag tcatcagtca ccagccagtc agtagtattt tt          52

<210> SEQ ID NO 4
<211> LENGTH: 57
<212> TYPE: DNA
<213> ORGANISM: Saccharum officinarum

<400> SEQUENCE: 4
gtcaatttgc ttaataagag tagcgtctgc taacaccata tacagaatga ttccggc     57

<210> SEQ ID NO 5
<211> LENGTH: 57
<212> TYPE: DNA
<213> ORGANISM: Saccharum officinarum

<400> SEQUENCE: 5
taccaagaca gttagtgcag aagtatatgt cttcgactat agcaagcacc catctaa     57

<210> SEQ ID NO 6
<211> LENGTH: 50
<212> TYPE: DNA
<213> ORGANISM: Saccharum officinarum

<400> SEQUENCE: 6
cctgcacttt gtcgcagaag atggcgtaat cactaccttc aacgtcacgg             50

<210> SEQ ID NO 7
<211> LENGTH: 50
<212> TYPE: DNA
<213> ORGANISM: Saccharum officinarum

<400> SEQUENCE: 7
```

```
gccaccgcaa ccgtcactgg cacgccacag ctaatcaaga ctgaggtaga            50
```

<210> SEQ ID NO 8
<211> LENGTH: 50
<212> TYPE: DNA
<213> ORGANISM: Saccharum officinarum

<400> SEQUENCE: 8

```
cccacgatct tccagtgcct gctgctgttc atcacttcca gattcagaac            50
```

<210> SEQ ID NO 9
<211> LENGTH: 58
<212> TYPE: DNA
<213> ORGANISM: Saccharum officinarum

<400> SEQUENCE: 9

```
aacagagaaa ggagagagag aggaggatca gcagattact tcttacaaga gttaaaca   58
```

<210> SEQ ID NO 10
<211> LENGTH: 73
<212> TYPE: DNA
<213> ORGANISM: Saccharum officinarum

<400> SEQUENCE: 10

```
tgagtgattt tgggacatga cttagtttca gtgaaatgtt ttttttacta tatatgtaat   60
atgcacactg ctt                                                     73
```

<210> SEQ ID NO 11
<211> LENGTH: 72
<212> TYPE: DNA
<213> ORGANISM: Saccharum officinarum

<400> SEQUENCE: 11

```
attcacagca cgtggatcct ccaataagat caattccaca gtatttttat tcataataga   60
gtaaatttgt ct                                                      72
```

<210> SEQ ID NO 12
<211> LENGTH: 50
<212> TYPE: DNA
<213> ORGANISM: Saccharum officinarum

<400> SEQUENCE: 12

```
cccgggagtg ggtgcgacca tgcgagtcga gtcgtgtggt ggggtggtct             50
```

<210> SEQ ID NO 13
<211> LENGTH: 50
<212> TYPE: DNA
<213> ORGANISM: Saccharum officinarum

<400> SEQUENCE: 13

```
atgacgaagc caacagaggt tgctatgcag tccaagaaca atgaacttgc             50
```

<210> SEQ ID NO 14
<211> LENGTH: 67
<212> TYPE: DNA
<213> ORGANISM: Saccharum officinarum

<400> SEQUENCE: 14

```
tgattggaac caaaaaattc acatcaaaca ggtcagtttc catatgaact cggaaacttt   60
gtgtgta                                                            67
```

```
<210> SEQ ID NO 15
<211> LENGTH: 52
<212> TYPE: DNA
<213> ORGANISM: Saccharum officinarum

<400> SEQUENCE: 15
tcacttgtaa ctcactggca ttgtaaacta tgcagataag agcacagcac tg          52

<210> SEQ ID NO 16
<211> LENGTH: 50
<212> TYPE: DNA
<213> ORGANISM: Saccharum officinarum

<400> SEQUENCE: 16
tggacttgct tctgtacaaa gtccgtgtgt cgcggctgct ccctgcaaca             50

<210> SEQ ID NO 17
<211> LENGTH: 18
<212> TYPE: DNA
<213> ORGANISM: Artificial Sequence
<220> FEATURE:
<223> OTHER INFORMATION: Synthetic DNA

<400> SEQUENCE: 17
cacgatggat ccagtgca                                                18

<210> SEQ ID NO 18
<211> LENGTH: 16
<212> TYPE: DNA
<213> ORGANISM: Artificial Sequence
<220> FEATURE:
<223> OTHER INFORMATION: Synthetic DNA

<400> SEQUENCE: 18
ctggatccat cgtgca                                                  16

<210> SEQ ID NO 19
<211> LENGTH: 16
<212> TYPE: DNA
<213> ORGANISM: Artificial Sequence
<220> FEATURE:
<223> OTHER INFORMATION: Synthetic DNA

<400> SEQUENCE: 19
gatggatcca gtgcag                                                  16
```

SUGARCANE-STALK-SUGAR-CONTENT-RELATED MARKER AND THE USE THEREOF

CROSS REFERENCE TO RELATED APPLICATIONS

This application is a Divisional Application of U.S. application Ser. No. 13/988,711 filed May 21, 2013, which is a National Stage of International Application No. PCT/JP2011/006685 filed Nov. 30, 2011, claiming priority based on Japanese Patent Application No. 2010-270769 filed Dec. 3, 2010, the contents of all of which are incorporated herein by reference in their entirety.

TECHNICAL FIELD

The present invention relates to a stalk-sugar-content-related marker whereby a sugarcane line characterized by an increase in stalk sugar content can be selected, and a method for use thereof.

BACKGROUND ART

Sugarcane has been cultivated as a raw material for sugar, liquor, and the like for edible use. In addition, sugarcane has been used as, for example, a raw material for biofuel in a variety of industrial fields. Under such circumstances, there is a need to develop novel sugarcane varieties having desirable characteristics (e.g., sugar content, enhanced vegetative capacity, sprouting capacity, disease resistance, insect resistance, cold resistance, an increase in leaf blade length or leaf area, and an increase in stalk length or stalk weight).

In general, the following three ways may be used for identification of a plant variety/line: "characteristics comparison" for comparison of characteristics data, "comparison during cultivation" for comparison of plants cultivated under the same conditions, and "DNA assay" for DNA analysis. There are many problems in line identification with characteristics comparison or comparison during cultivation, including reduction of precision due to differences in cultivation conditions, lengthy duration of field research that requires a number of steps, and the like. In particular, since sugarcane plants are much larger than other graminaceous crops such as rice and maize, it has been difficult to conduct line identification based on field research. In addition, in order to identify a variety/line having distinct characteristics in terms of leaf blade length, leaf area, stalk length, stalk weight, and the like, it is necessary to collect such characteristic data after long-term cultivation of sugarcane. In addition, even after long-term cultivation of sugarcane, it is difficult to identify such line with high accuracy because such characteristics are environmentally susceptible.

Further, for creation of a novel sugarcane variety, first, tens of thousands of seedlings are created via crossing, followed by seedling selection and stepwise selection of excellent lines. Eventually, 2 or 3 types of novel varieties having desired characteristics can be obtained. As described above, for creation of a novel sugarcane variety, it is necessary to cultivate and evaluate an enormous number of lines, and it is also necessary to prepare a large-scale field and make highly time-consuming efforts.

Therefore, it has been required to develop a method for identifying a sugarcane line having desired characteristics with the use of markers present in the sugarcane genome. In particular, upon creation of a novel sugarcane variety, if excellent markers could be used to examine a variety of characteristics, the above problems particular to sugarcane would be resolved, and the markers would be able to serve as very effective tools. However, since sugarcane plants have a large number of chromosomes (approximately 100 to 130) due to higher polyploidy, the development of marker technology has been slow. In the case of sugarcane, although the USDA reported genotyping with the use of SSR markers (Non-Patent Document 1), the precision of genotyping is low because of the small numbers of markers and polymorphisms in each marker. In addition, the above genotyping is available only for American/Australian varieties, and therefore it cannot be used for identification of the major varieties cultivated in Japan, Taiwan, India, and other countries or lines that serve as useful genetic resources.

In addition, Non-Patent Document 2 suggests the possibility that a sugarcane genetic map can be created by increasing the number of markers, comparing individual markers in terms of a characteristic relationship, and verifying the results. However, in Non-Patent Document 2, an insufficient number of markers are disclosed and markers linked to desired characteristics have not been found.

CITATION LIST

Non Patent Literature

NPL 1: Maydica 48 (2003) 319-329 "Molecular genotyping of sugarcane clones with microsatellite DNA markers"
NPL 2: Nathalie Piperidis et al., Molecular Breeding, 2008, Vol. 21, 233-247

SUMMARY OF INVENTION

Technical Problem

In view of the above, an object of the present invention is to provide a marker related to stalk sugar content, which is a quantitative trait of sugarcane.

Solution to Problem

In order to achieve the object, the present inventors conducted intensive studies. The present inventors prepared many sugarcane markers and carried out linkage analysis of quantitative traits along with such markers for hybrid progeny lines. Accordingly, the present inventors found markers linked to quantitative traits such as an increase in stalk sugar content. This has led to the completion of the present invention.

The present invention encompasses the following.

(1) A sugarcane-stalk-sugar-content-related marker, which consists of a continuous nucleic acid region existing in a region sandwiched between the nucleotide sequence shown in SEQ ID NO: 1 and the nucleotide sequence shown in SEQ ID NO: 8 or a region sandwiched between the nucleotide sequence shown in SEQ ID NO: 9 and the nucleotide sequence shown in SEQ ID NO: 16 of a sugarcane chromosome.

(2) The sugarcane-stalk-sugar-content-related marker according to (1), wherein the continuous nucleic acid region comprises any nucleotide sequence selected from the group consisting of the nucleotide sequences shown in SEQ ID NOS: 1 to 16.

(3) The sugarcane-stalk-sugar-content-related marker according to (1), wherein the continuous nucleic acid region is located at a position in a region sandwiched between the nucleotide sequence shown in SEQ ID NO: 1 and the nucleotide sequence shown in SEQ ID NO: 2 or a region sandwiched between the nucleotide sequence shown in SEQ ID NO: 13 and the nucleotide sequence shown in SEQ ID NO: 14 of a sugarcane chromosome.

(4) A method for producing a sugarcane line having an increased stalk sugar content comprising: a step of extracting a chromosome of a progeny plant obtained from parent plants, at least one of which is sugarcane; and a step of determining the presence or absence of the sugarcane-stalk-sugar-content-related marker according to any one of (1) to (3) in the obtained sugarcane chromosome.

(5) The method for producing a sugarcane line according to (4), wherein a DNA chip provided with probes each corresponding to the sugarcane-stalk-sugar-content-related marker is used in the determination step.

(6) The method for producing a sugarcane line according to (4), wherein the progeny plant is in the form of seeds or a young seedling and the chromosome is extracted from the seeds or the young seedling.

A part or all of the content disclosed in the description and/or drawings of Japanese Patent Application No. 2010-270769, which is a priority document of the present application, is herein incorporated by reference.

Advantageous Effects of Invention

According to the present invention, a novel sugarcane-stalk-sugar-content-related marker linked to a sugarcane quantitative trait such as an increase in stalk sugar content can be provided. With the use of the sugarcane-stalk-sugar-content-related marker of the present invention, the stalk sugar content of a line obtained by crossing sugarcane lines can be identified. Thus, a sugarcane line characterized by an increase in stalk sugar content can be identified at a very low cost.

DESCRIPTION OF EMBODIMENTS

Figure 1:
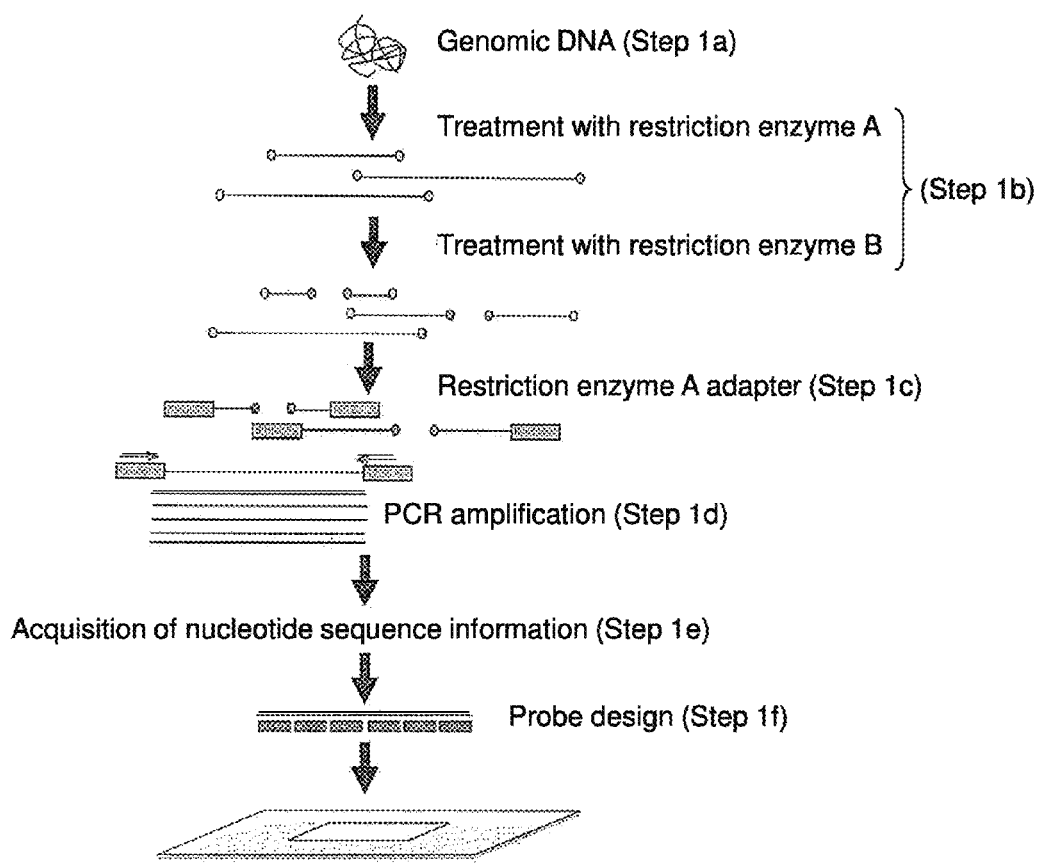
FIG. 1 schematically shows the process of production of a DNA microarray used for acquisition of sugarcane chromosome markers.

The sugarcane-stalk-sugar-content-related marker and the method for using the same according to the present invention are described below. In particular, a method for producing a sugarcane line using a sugarcane-stalk-sugar-content-related marker is described.

Sugarcane-Stalk-Sugar-Content-Related Markers

The sugarcane-stalk-sugar-content-related marker of the present invention corresponds to a specific region present on a sugarcane chromosome and is linked to causative genes (i.e., gene group) for a trait that causes an increase in sugarcane stalk sugar content. Thus, it can be used to identify a trait characterized by an increase in sugarcane stalk sugar content. Specifically, it is possible to determine that a progeny line obtained using a known sugarcane line is a line having a trait characterized by an increase in stalk sugar content by confirming the presence of a sugarcane-stalk-sugar-content-related marker in such progeny line.

Here, the term "stalk sugar content" refers to the sugar content in juice extracted from stalks of a single individual of sugarcane. The term "stalk sugar content" corresponds to the Brix value of juice, which can be measured by a known method for sugar content measurement (using, for example, a refractometer (Brix meter)), in the Examples described below. The Brix value indicates the content of soluble solids such as sucrose or reducing sugar in sugarcane juice. Therefore, there is a correlation between the Brix value and the stalk sugar content. Accordingly, if the Brix value is high, it can be determined that the stalk sugar content is also high.

The term "sugarcane" used herein refers to a plant belonging to the genus *Saccharum* of the family Poaceae. In addition, the term "sugarcane" includes both so-called noble cane (scientific name: *Saccharum officinarum*) and wild cane (scientific name: *Saccharum spontaneum*). The term "known sugarcane variety/line" is not particularly limited. It includes any variety/line capable of being used in Japan and any variety/line used outside Japan. Examples of sugarcane varieties cultivated in Japan include, but are not limited to, Ni1, NiN2, NiF3, NiF4, NiF5, Ni6, NiN7, NiF8, Ni9, NiTn10, Ni11, Ni12, Ni14, Ni15, Ni16, Ni17, NiTn19, NiTn20, Ni22, and Ni23. Examples of main sugarcane varieties used in Japan described herein include, but are not limited to, NiF8, Ni9, NiTn10, and Ni15. In addition, examples of main sugarcane varieties that have been introduced into Japan include, but are not limited to, F177, Nco310, and F172. In addition, a progeny line may be a line obtained by crossing a mother plant and a father plant of the same species, each of which is a sugarcane variety/line, or it may be a hybrid line obtained from parent plants when one thereof is a sugarcane variety/line and the other is a closely related variety/line (*Erianthus arundinaceus*). In addition, a progeny line may be obtained by so-called backcrossing.

The sugarcane-stalk-sugar-content-related marker of the present invention has been newly identified by QTL (Quantitative Trait Loci) analysis using a genetic linkage map containing 3004 markers originally obtained from chromosomes of the NiF8 sugarcane variety, a genetic linkage map containing 4569 markers originally obtained from chromosomes of the Ni9 sugarcane variety, and sugarcane stalk sugar content data. In addition, many genes are presumably associated with the sugarcane stalk sugar content, which is a quantitative trait characterized by a continuous distribution of stalk sugar content values. For QTL analysis, the QTL Cartographer gene analysis software (Wang S., C. J. Basten, and Z.-B. Zeng (2010); Windows QTL Cartographer 2.5. Department of Statistics, North Carolina State University, Raleigh, N.C.) is used, and the analysis is carried out by the composite interval mapping (CIM) method.

Specifically, peaks with LOD scores equivalent to or exceeding a given threshold (e.g., 3.0) have been found in a region included in the above genetic linkage maps by QTL analysis described above. That is, the following 2 regions having such peaks have been specified: an approximately 17.5-cM (centimorgan) region (the NiF8 sugarcane variety);

and an approximately 24.6-cM region (the Ni9 sugarcane variety). The term "morgan (M)" used herein refers to a unit representing the relative distance between genes on a chromosome, and it is expressed by the percentage of the crossover rate. In a case of a sugarcane chromosome, 1 cM corresponds to approximately 2000 kb. In addition, it is suggested that causative genes (i.e., gene group) for a trait that causes an increase in stalk sugar content could be present at the peak positions or in the vicinity thereof.

The 17.5-cM region having the above peak of the NiF8 sugarcane variety is a region that comprises 8 types of markers listed in table 1 below in the order shown in table 1.

TABLE 1

| Linkage group | Marker name | Nucleotide sequence information | Signal threshold | SEQ ID NO |
|---|---|---|---|---|
| NiF8_53 | N804812 | GGTTCGTCAAGGCCAAGGCGGCGGCGCTGGTCGGAGCG CACAAGGTGAAG | 2,000 | SEQ ID NO 1 |
|  | N826007 | ATGTATAGATGACATAAGAAAGGATGTAATCACTTAACT GATGCTTACTAGATTATTAAGCAAATATAATAGGTA | 1,000 | SEQ ID NO 2 |
|  | N826674 | TTCAGCACATTCAGCACTAGTCATCAGTCACCAGCCAGT CAGTAGTATTTTT | 2,500 | SEQ ID NO 3 |
|  | N821523 | GTCAATTTGCTTAATAAGAGTAGCGTCTGCTAACACCAT ATACAGAATGATTCCGGC | 1,000 | SEQ ID NO 4 |
|  | N802816 | TACCAAGACAGTTAGTGCAGAAGTATATGTCTTCGACTA TAGCAAGCACCOATCTAA | 1,000 | SEQ ID NO 5 |
|  | N829577 | CCTGCACTTTGTCGCAGAAGATGGCGTAATCACTACCTT CAACGTCACGG | 1,500 | SEQ ID NO 6 |
|  | N826565 | GCCACCGCAACCGTCACTGGCACGCCACAGCTAATCAA GACTGAGGTAGA | 2,000 | SEQ ID NO 7 |
|  | N819380 | CCCACGATCTTCCAGTGCCTGCTGCTGTTCATCACTTCC AGATTCAGAAC | 1,000 | SEQ ID NO 8 |

The 24.6-cM region having the above peak of the Ni9 sugarcane variety is a region that comprises 8 types of markers listed in table 2 below in the order shown in table 2.

TABLE 2

| Linkage group | Marker name | Nucleotide sequence information | Signal threshold | SEQ ID NO |
|---|---|---|---|---|
| Ni9_61 | N918150 | AACAGAGAAAGGAGAGAGAGAGGAGGATCAGCAGATTA CTTCTTACAAGAGTTAAACA | 1,500 | SEQ ID NO 9 |
|  | N917916 | TGAGTGATTTTGGGACATGACTTAGTTTCAGTGAAATGT TTTTTTACTATATATGTAATATGCACACTGCTT | 2,000 | SEQ ID NO 10 |
|  | N915803 | ATTCACAGCACGTGGATCCTCCAATAAGATCAATTCCAC AGTATTTTATTCATAATAGAGTAAATTTGTCT | 2,000 | SEQ ID NO 11 |
|  | N910211 | CCCGGGAGTGGGTGCGACCATGCGAGTCAGTCGTGTG GTGGGGTGGTCT | 1,000 | SEQ ID NO 12 |
|  | N900644 | ATGACGAAGCCAACAGAGGTTGCTATGCAGTCCAAGAA CAATGAACTTGC | 1,000 | SEQ ID NO 13 |
|  | N921335 | TGATTGGAACCAAAAAATTCACATCAAACAGGTCAGTTT CCATATGAAOCTCGGAAACTTTGTGTGTA | 1,000 | SEQ ID NO 14 |
|  | N901390 | TCACTTGTAACTCACTGGCATTGTAAACTATGCAGATAA GAGCACAGCACTG | 1,000 | SEQ ID NO 15 |
|  | N915049 | TGGACTTGCTTCTGTACAAAGTCCGTGTGTCGCGGCTGD TCCTGCAACA | 1,000 | SEQ ID NO 16 |

In addition, in tables 1 and 2, "Linkage group" represents the number given to each group among a plurality of linkage groups specified by QTL analysis. In tables 1 and 2, "Marker name" represents the name given to each marker originally obtained in the present invention. In tables 1 and 2, "Signal threshold" represents a threshold used for determination of the presence or absence of a marker.

The peak contained in the 17.5-cM region of the NiF8 sugarcane variety is present in a region sandwiched between a marker (N804812) consisting of the nucleotide sequence shown in SEQ ID NO: 1 and a marker (N826007) consisting of the nucleotide sequence shown in SEQ ID NO: 2.

In addition, the peak contained in the 24.6-cM region of the Ni9 sugarcane variety is present in a region sandwiched between a marker (N900644) consisting of the nucleotide sequence shown in SEQ ID NO: 13 and a marker (N921335) consisting of the nucleotide sequence shown in SEQ ID NO: 14.

A continuous nucleic acid region existing in any of 2 regions containing markers shown in tables 1 and 2 can be used as a sugarcane-stalk-sugar-content-related marker. The term "nucleic acid region" used herein refers to a region having a nucleotide sequence having 95% or less, preferably 90% or less, more preferably 80% or less, and most preferably 70% or less identity to a different region present on a sugarcane chromosome. If the identity of a nucleic acid region serving as a sugarcane-stalk-sugar-content-related marker to a different region falls within the above range, the nucleic acid region can be specifically detected according to a standard method. The identity level described herein can be calculated using default parameters and BLAST or a similar algorithm.

In addition, the base length of a nucleic acid region serving as a sugarcane-stalk-sugar-content-related marker can be at least 8 bases, preferably 15 bases or more, more preferably 20 bases or more, and most preferably 30 bases. If the base length of a nucleic acid region serving as a sugarcane-stalk-sugar-content-related marker falls within the above range, the nucleic acid region can be specifically detected according to a standard method.

In particular, among the 8 types of markers contained in the 17.5-cM region of the NiF8 sugarcane variety, a sugarcane-stalk-sugar-content-related marker is preferably designated as existing in the region sandwiched between the nucleotide sequence shown in SEQ ID NO: 1 and the nucleotide sequence shown in SEQ ID NO: 2. This is because the above peak is present in the region sandwiched between the nucleotide sequence shown in SEQ ID NO: 1 and the nucleotide sequence shown in SEQ ID NO: 2. In addition, among the 8 types of markers contained in the 24.6-cM region of the Ni9 sugarcane variety, a sugarcane-stalk-sugar-content-related marker is preferably designated as existing in the region sandwiched between the nucleotide sequence shown in SEQ ID NO: 13 and the nucleotide sequence shown in SEQ ID NO: 14. This is because the above peak is present in the region sandwiched between the nucleotide sequence shown in SEQ ID NO: 13 and the nucleotide sequence shown in SEQ ID NO: 14.

In addition, a nucleic acid region containing a single marker selected from among the 16 types of markers shown in tables 1 and 2 can be used as a sugarcane-stalk-sugar-content-related marker. For example, it is preferable to use, as a sugarcane-stalk-sugar-content-related marker, a nucleic acid region containing a marker (N826007) consisting of the nucleotide sequence shown in SEQ ID NO: 2 located closest to the peak position in the 17.5-cM region of the NiF8 sugarcane variety or a nucleic acid region containing a marker (N921335) consisting of the nucleotide sequence shown in SEQ ID NO: 14 located closest to the peak position in the 24.6-cM region of the Ni9 sugarcane variety. In such case, the nucleotide sequence of a nucleic acid region containing the marker can be specified by inverse PCR using primers designed based on the nucleotide sequence of such marker.

Further, as a sugarcane-stalk-sugar-content-related marker, any of the above 16 types of markers can be directly used. Specifically, one or more type(s) of markers selected from among the 16 types of such markers can be directly used as a sugarcane-stalk-sugar-content-related marker. For example, it is preferable to use, as a sugarcane-stalk-sugar-content-related marker, a marker (N826007) consisting of the nucleotide sequence shown in SEQ ID NO: 2 located closest to the peak position in the 17.5-cM region of the NiF8 sugarcane variety or a marker (N921335) consisting of the nucleotide sequence shown in SEQ ID NO: 14 closest to the peak position in the 24.6-cM region of the Ni9 sugarcane variety.

Sugarcane Marker Identification

As described above, sugarcane-stalk-sugar-content-related markers were identified from among 3004 markers originally obtained from chromosomes of the NiF8 sugarcane variety and 4569 markers originally obtained from chromosomes of the Ni9 sugarcane variety in the present invention. These markers are described below. Upon identification of these markers, a DNA microarray can be used according to the method disclosed in JP Patent Application No. 2009-283430.

Specifically, these markers originally obtained from sugarcane chromosomes are used with a DNA microarray having probes designed by the method disclosed in JP Patent Application No. 2009-283430. The method for designing probes as shown in FIG. 1 is described below. First, genomic DNA is extracted from sugarcane (step 1a). Next, the extracted genomic DNA is digested with a single or a plurality of restriction enzyme(s) (step 1b). In addition, in the example shown in FIG. 1, 2 types of restriction enzymes illustrated as restriction enzymes A and B are used (in the order of A first and then B) to digest genomic DNA. The restriction enzymes used herein are not particularly limited. However, examples of restriction enzymes that can be used include PstI, EcoRI, HindIII, BstNI, HpaII, and HaeIII. In particular, restriction enzymes can be adequately selected in consideration of the frequency of appearance of recognition sequences such that a genomic DNA fragment having a base length of 20 to 10000 can be obtained when genomic DNA is completely digested. In addition, when a plurality of restriction enzymes are used, it is preferable for a genomic DNA fragment obtained after the use of all restriction enzymes to have a base length of 200 to 6000. Further, when a plurality of restriction enzymes are used, the order in which restriction enzymes are subjected to treatment is not particularly limited. In addition, a plurality of restriction enzymes may be used in an identical reaction system if they are treated under identical conditions (e.g., solution composition and temperature). Specifically, in the example shown in FIG. 1, genomic DNA is digested using restriction enzymes A and B in such order. However, genomic DNA may be digested by simultaneously using restriction enzymes A and B in an identical reaction system. Alternatively, genomic DNA may be digested using restriction enzymes B and A in such order. Further, 3 or more restriction enzymes may be used.

Next, adapters are bound to a genomic DNA fragment subjected to restriction enzyme treatment (step 1c). The adapter used herein is not particularly limited as long as it can be bound to both ends of a genomic DNA fragment obtained by the above restriction enzyme treatment. For example, it is possible to use, as an adapter, an adapter having a single strand complementary to a protruding end (sticky end) formed at each end of genomic DNA by restriction enzyme treatment and a primer binding sequence to which a primer used upon amplification treatment as described in detail below can hybridize. In addition, it is also possible to use, as an adapter, an adapter having a single strand complementary to the above protruding end (sticky end) and a restriction enzyme recognition site that is incorporated into a vector upon cloning.

In addition, when genomic DNA is digested using a plurality of restriction enzymes, a plurality of adapters corresponding to the relevant restriction enzymes can be prepared and used. Specifically, it is possible to use a plurality of adapters having single strands complementary to different protruding ends formed upon digestion of genomic DNA with a plurality of restriction enzymes. Here, a plurality of adapters corresponding to a plurality of restriction enzymes each may have a common primer binding sequence such that a common primer can hybridize to each such adapter. Alternatively, they may have different primer binding sequences such that different primers can separately hybridize thereto.

Further, when genomic DNA is digested using a plurality of restriction enzymes, it is possible to use, as an adaptor, adapter(s) corresponding to one or more restriction enzyme(s) selected from among a plurality of the used restriction enzymes.

Next, a genomic DNA fragment to both ends of which adapters have been added is amplified (step 1d). When an adapter having a primer binding sequence is used, the genomic DNA fragment can be amplified using a primer that can hybridize to the primer binding sequence. Alternatively, a genomic DNA fragment to which an adapter has been added is cloned into a vector using the adapter sequence. The genomic DNA fragment can be amplified using primers that can hybridize to specific regions of the vector. In addition, as an example, PCR can be used for a genomic DNA fragment amplification reaction using primers.

In addition, when genomic DNA is digested using a plurality of restriction enzymes and a plurality of adapters corresponding to the relevant restriction enzymes are ligated to genomic DNA fragments, the adapters are ligated to all genomic DNA fragments obtained by treatment with a plurality of restriction enzymes. In this case, all the obtained genomic DNA fragments can be amplified by carrying out a nucleic acid amplification reaction using primer binding sequences contained in adapters.

Alternatively, genomic DNA is digested using a plurality of restriction enzymes, followed by ligation of adapter(s) corresponding to one or more restriction enzyme(s) selected from among a plurality of the used restriction enzymes to genomic DNA fragments. In such case, among the obtained genomic DNA fragments, a genomic DNA fragment to both ends of which the selected restriction enzyme recognition sequences have been ligated can be exclusively amplified.

Next, the nucleotide sequence of the amplified genomic DNA fragment is determined (step 1e). Then, at least one region, which has a base length shorter than the base length of the genomic DNA fragment and corresponds to at least a partial region of the genomic DNA fragment, is specified. Sugarcane probes are designed using at least one of the thus specified regions (step 1f). A method for determining the nucleotide sequence of a genomic DNA fragment is not particularly limited. A conventionally known method using a DNA sequencer applied to the Sanger method or the like can be used. For example, a region to be designed herein has a 20- to 100-base length, preferably a 30- to 90-base length, and more preferably a 50- to 75-base length as described above.

As described above, a DNA microarray can be produced by designing many probes using genomic DNA extracted from sugarcane and synthesizing an oligonucleotide having a desired nucleotide sequence on a support based on the nucleotide sequence of the designed probe. With the use of a DNA microarray prepared as described above, 3004 markers and 4569 markers, including the above 16 types of sugarcane-stalk-sugar-content-related markers shown in SEQ ID NOS: 1 to 16, can be identified from the sugarcane varieties NiF8 and Ni9, respectively.

More specifically, the present inventors obtained signal data of known sugarcane Varieties (NiF8 and Ni9) and a progeny line (line 191) obtained by crossing the varieties with the use of the DNA microarray described above. Then, genotype data were obtained based on the obtained signal data. Based on the obtained genotype data, chromosomal marker position information was obtained by calculation using the gene distance function (Kosambi) and the AntMap genetic map creation software (Iwata H, Ninomiya S (2006) AntMap: constructing genetic linkage maps using an ant colony optimization algorithm, Breed Sci 56: 371-378). Further, a genetic map datasheet was created based on the obtained marker position information using Mapmaker/EXP ver. 3.0 (A Whitehead Institute for Biomedical Research Technical Report, Third Edition, January, 1993). As a result, 3004 markers and 4569 markers, including the afore-mentioned 16 types of sugarcane-stalk-sugar-content-related markers shown in SEQ ID NOS: 1 to 16, were identified from the sugarcane varieties NiF8 and Ni9, respectively.

Use of Sugarcane-Stalk-Sugar-Content-Related Markers

The use of sugarcane-stalk-sugar-content-related markers makes it possible to determine whether a sugarcane progeny line or the like, which has a phenotype exhibiting unknown stalk sugar content, is a line having a phenotype showing an increase in stalk sugar content. The expression "the use of sugarcane-stalk-sugar-content-related markers" used herein indicates the use of a DNA microarray having probes corresponding to sugarcane-stalk-sugar-content-related markers in one embodiment. The expression "probes corresponding to sugarcane-stalk-sugar-content-related markers" indicates oligonucleotides that can specifically hybridize under stringent conditions to sugarcane-stalk-sugar-content-related markers defined as above. For instance, such oligonucleotides can be designed as partial or whole regions with base lengths of at least 10 continuous bases, 15 continuous bases, 20 continuous bases, 25 continuous bases, 30 continuous bases, 35 continuous bases, 40 continuous bases, 45 continuous bases, or 50 or more continuous bases of the nucleotide sequences or complementary strands thereof of sugarcane-stalk-sugar-content-related markers defined as above. In addition, a DNA microarray having such probes may be any type of microarray, such as a microarray having a planar substrate comprising glass, silicone, or the like as a carrier, a bead array comprising microbeads as carriers, or a three-dimensional microarray having an inner wall comprising hollow fibers to which probes are fixed. The use of a DNA microarray prepared as described above makes it possible to determine whether a sugarcane line such as a progeny line or the like, which has a phenotype exhibiting unknown stalk sugar content, is a line having a phenotype showing an increase in stalk sugar content. In addition, in the case of a method other than the above method involving the use of a DNA microarray, it is also possible to determine whether a sugarcane line, which has a phenotype exhibiting unknown stalk sugar content, is a line having a trait characterized by an increase in stalk sugar content by detecting the above sugarcane-stalk-sugar-content-related markers by a conventionally known method.

Figure 2:
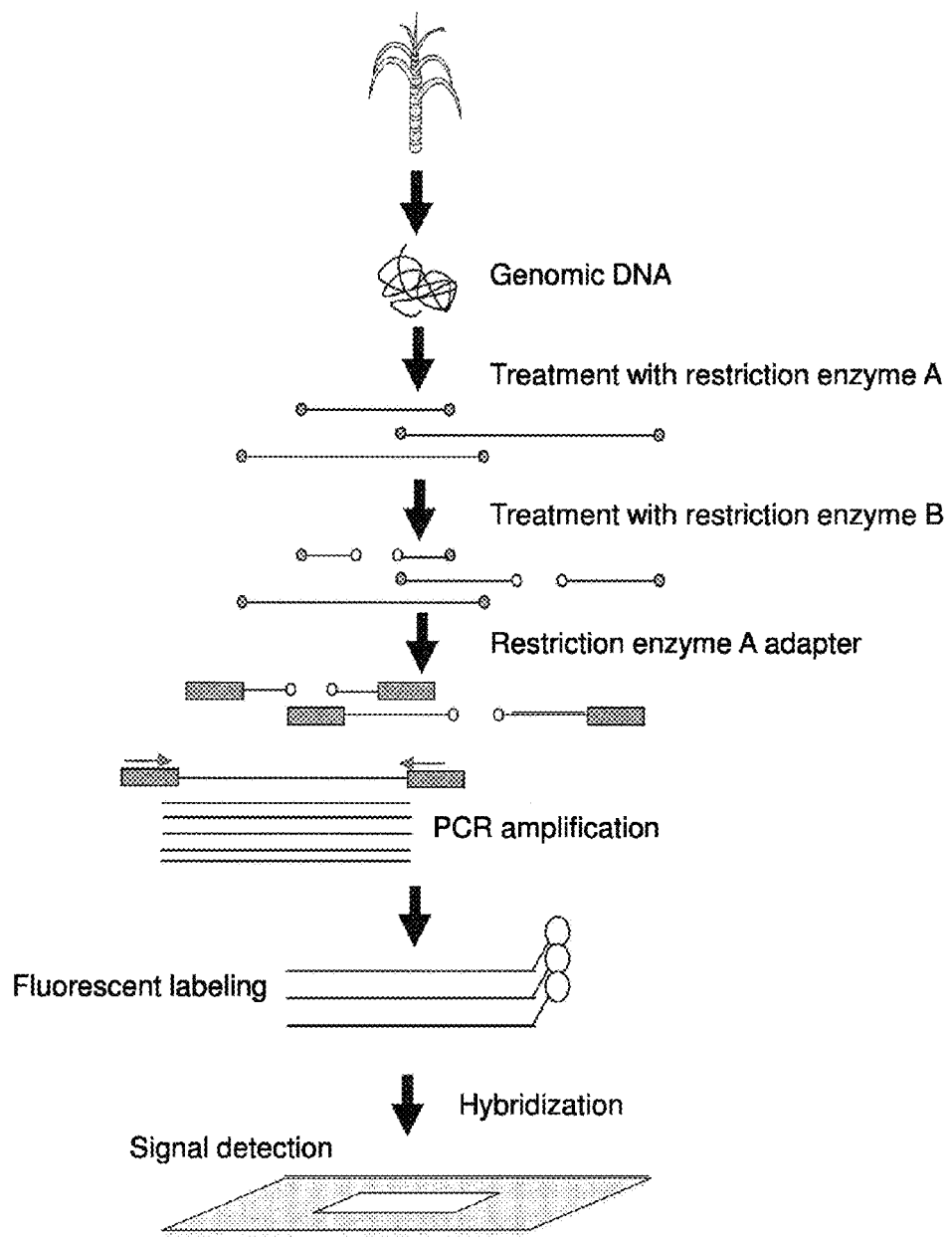
FIG. 2 schematically shows a step of signal detection with the use of a DNA microarray.

The method involving the use of a DNA microarray is described in more detail. As shown in FIG. 2, first, genomic DNA is extracted from a sugarcane sample. In this case, a sugarcane sample is a sugarcane line such as a sugarcane progeny line, which has a phenotype exhibiting unknown stalk sugar content, and thus which can be used as a subject to be determined whether to have a trait characterized by an increase in stalk sugar content or not. Next, a plurality of genomic DNA fragments are prepared by digesting the extracted genomic DNA with restriction enzymes used for preparing the DNA microarray. Then, the obtained genomic DNA fragments are ligated to adapters used for preparation of the DNA microarray. Subsequently, the genomic DNA fragments, to both ends of which adapters have been added, are amplified using primers employed for preparation of the DNA microarray. Accordingly, sugarcane-sample-derived genomic DNA fragments corresponding to the genomic DNA fragments amplified in step 1d upon preparation of the DNA microarray can be amplified.

In this step, among the genomic DNA fragments to which adapters have been added, specific genomic DNA fragments may be selectively amplified. For instance, in a case in which a plurality of adapters corresponding to a plurality of restriction enzymes are used, genomic DNA fragments to which specific adapters have been added can be selectively amplified. In addition, when genomic DNA is digested with a plurality of restriction enzymes, genomic DNA fragments to which adapters have been added can be selectively amplified by adding adapters only to genomic DNA fragments that have protruding ends corresponding to specific restriction enzymes among the obtained genomic DNA fragments. Thus, specific DNA fragment concentration can be increased by selectively amplifying the specific genomic DNA fragments.

Thereafter, amplified genomic DNA fragments are labeled. Any conventionally known substance may be used as a labeling substance. Examples of a labeling substance that can be used include fluorescent molecules, dye molecules, and radioactive molecules. In addition, this step can be omitted using a labeled nucleotide in the step of amplifying genomic DNA fragments. This is because when genomic DNA fragments are amplified using a labeled nucleotide in the amplification step, amplified DNA fragments can be labeled.

Next, labeled genomic DNA fragments are allowed to come into contact with the DNA microarray under certain conditions such that probes fixed to the DNA microarray hybridize to the labeled genomic DNA fragments. At such time, preferably, highly stringent conditions are provided for hybridization. Under highly stringent conditions, it becomes possible to determine with high accuracy whether or not sugarcane-stalk-sugar-content-related markers are present in a sugarcane sample. In addition, stringent conditions can be adjusted based on reaction temperature and salt concentration. That is, an increase in temperature or a decrease in salt concentration results in more stringent conditions. For example, when a probe having a length of 50 to 75 bases is used, the following more stringent conditions can be provided as hybridization conditions: 40 degrees C. to 44 degrees C.; 0.2 SDS; and 6×SSC.

In addition, hybridization between labeled genomic DNA fragments and probes can be confirmed by detecting a labeling substance. Specifically, after the above hybridization reaction of labeled genomic DNA fragments and probes, unreacted genomic DNA fragments and the like are washed, and the labeling substance bound to each genomic DNA fragment specifically hybridizing to a probe is observed. For instance, in a case in which the labeling substance is a fluorescent material, the fluorescence wavelength is detected. In a case in which the labeling substance is a dye molecule, the dye wavelength is detected. More specifically, apparatuses such as fluorescent detectors and image analyzers used for conventional DNA microarray analysis can be used.

As described above, it is possible to determine whether or not a sugarcane sample has the above sugarcane-stalk-sugar-content-related marker(s) with the use of a DNA microarray. In particular, according to the method described above, it is not necessary to cultivate a sugarcane sample to such an extent that determination of the actual stalk sugar content thereof becomes possible. For instance, seeds of a progeny line or a young seedling obtained as a result of germination of such seeds can be used. Therefore, the area of a field used for cultivation of a sugarcane sample and other factors such as cost of cultivation can be significantly reduced with the use of the sugarcane-stalk-sugar-content-related marker(s).

In particular, when a novel sugarcane variety is created, it is preferable to produce several tens of thousands of seedlings via crossing and then to identify a novel sugarcane variety using sugarcane-stalk-sugar-content-related markers prior to or instead of seedling selection. The use of such sugarcane-stalk-sugar-content-related marker(s) makes it possible to significantly reduce the number of excellent lines that need to be cultivated in an actual field. This allows drastic reduction of time-consuming efforts and the cost required to create a novel sugarcane variety.

Causative genes (i.e., gene group) for a trait that causes an increase in sugarcane stalk sugar content can be isolated using the above sugarcane-stalk-sugar-content-related markers. A conventionally known method can be used as an isolation method (see "Illustrated bio-experiment practice 4 (Bio-Jikken Illustrated 4): Effortless Cloning," Kazuhiro Makabe (1997), Shujunsha Co., Ltd.). For example, causative genes for a trait that causes an increase in sugarcane stalk sugar content can be isolated by creating primers or probes corresponding to the above defined sugarcane-stalk-sugar-content-related markers and screening sugarcane genomic DNA or cDNA. In addition, a transformed plant characterized by an increase in stalk sugar content can be produced by transformation of plant cells using a recombinant vector including a causative gene for a trait that causes an increase in sugarcane stalk sugar content obtained above.

EXAMPLES

The present invention is hereafter described in greater detail with reference to the following examples, although the technical scope of the present invention is not limited thereto.

1. Production of DNA Microarray Probes
(1) Materials
The following varieties were used: sugarcane varieties: NiF8, Ni9, US56-15-8, POJ2878, Q165, R570, Co290 and B3439; closely-related sugarcane wild-type varieties: Glagah Kloet, Chunee, Natal Uba, and Robustum 9; and *Erianthus* varieties: IJ76-349 and JW630.

(2) Restriction Enzyme Treatment

Genomic DNA was extracted from each of the above sugarcane varieties, closely-related sugarcane wild-type varieties, and *Erianthus* varieties using DNeasy Plant Mini Kits (Qiagen). Genomic DNAs (750 ng each) were treated with a PstI restriction enzyme (NEB; 25 units) at 37 degrees C. for 2 hours. A BstNI restriction enzyme (NEB; 25 units) was added thereto, followed by treatment at 60 degrees C. for 2 hours.

(3) Adapter Ligation

PstI sequence adapters (5'-CACGATGGATCCAGTGCA-3' (SEQ ID NO: 17) and 5'-CTGGATCCATCGTGCA-3' (SEQ ID NO: 18)) and T4 DNA Ligase (NEB; 800 units) were added to the genomic DNA fragments treated in (2) (120 ng each), and the obtained mixtures were subjected to treatment at 16 degrees C. for 4 hours or longer. Thus, the adapters were selectively added to genomic DNA fragments having PstI recognition sequences at both ends thereof among the genomic DNA fragments treated in (2).

(4) PCR Amplification

A PstI sequence adapter recognition primer (5'-GATG-GATCCAGTGCAG-3' (SEQ ID NO: 19)) and Taq polymerase (TAKARA; PiimeSTAR; 1.25 units) were added to the genomic DNA fragment (15 ng) having the adaptors obtained in (3). Then, the genomic DNA fragment was amplified by PCR (treatment at 98 degrees C. for 10 seconds, 55 degrees C. for 15 seconds, 72 degrees C. for 1 minute for 30 cycles, and then at 72 degrees C. for 3 minutes, followed by storage at 4 degrees C.).

(5) Genome Sequence Acquisition

The nucleotide sequence of the genomic DNA fragment subjected to PCR amplification in (4) was determined by FLX454 (Roche) or the Sanger method. In addition, information on a nucleotide sequence sandwiched between PstI recognition sequences was obtained based on the total sorghum genome sequence information contained in the genome database (Gramene: http://www.gramene.org/).

(6) Probe Design and DNA Microarray Production 50- to 75-bp probes were designed based on the genome sequence information in (5). Based on the nucleotide sequence information of the designed probes, a DNA microarray having the probes was produced.

2. Acquisition of Signal Data Using a DNA Microarray (1) Materials

Sugarcane varieties/lines (NiF8 and Ni9) and the progeny line (line 191) were used.

(2) Restriction Enzyme Treatment

Genomic DNAs were extracted from NiF8, Ni9, and the progeny line (line 191) using DNeasy Plant Mini Kits (Qiagen). Genomic DNAs (750 ng each) were treated with a PstI restriction enzyme (NEB; 25 units) at 37 degrees C. for 2 hours. Then, a BstNI restriction enzyme (NEB; 25 units) was added thereto, followed by treatment at 60 degrees C. for 2 hours.

(3) Adapter Ligation

PstI sequence adapters (5'-CACGATGGATCCAGTGCA-3' (SEQ ID NO: 17) and 5'-CTGGATCCATCGTGCA-3' (SEQ ID NO: 18)) and T4 DNA Ligase (NEB; 800 units) were added to the genomic DNA fragments treated in (2) (120 ng each), and the obtained mixtures were treated at 16 degrees C. for 4 hours or longer. Thus, the adaptors were selectively added to a genomic DNA fragment having PstI recognition sequences at both ends thereof among the genomic DNA fragments treated in (2).

(4) PCR Amplification

A PstI sequence adapter recognition primer (5'-GATG-GATCCAGTGCAG-3' (SEQ ID NO: 19)) and Taq polymerase (TAKARA; PrimeSTAR; 1.25 units) were added to the genomic DNA fragment (15 ng) having the adapters obtained in (3). Then, the genomic DNA fragment was amplified by PCR (treatment at 98 degrees C. for 10 seconds, 55 degrees C. for 15 seconds, 72 degrees C. for 1 minute for 30 cycles, and then 72 degrees C. for 3 minutes, followed by storage at 4 degrees C.).

(5) Labeling

The PCR amplification fragment obtained in (4) above was purified with a column (Qiagen). Cy3 9mer wobble (TriLink; 1 O.D.) was added thereto. The resultant was treated at 98 degrees C. for 10 minutes and allowed to stand still on ice for 10 minutes. Then, Klenow (NEB; 100 units) was added thereto, followed by treatment at 37 degrees C. for 2 hours. Thereafter, a labeled sample was prepared by isopropanol precipitation.

(6) Hybridization/Signal Detection

The labeled sample obtained in (5) was subjected to hybridization using the DNA microarray prepared in 1 above in accordance with the NimbleGen Array User's Guide. Signals from the label were detected.

3. Identification of QTL for Sugarcane Stalk Sugar Content and Development of Markers (1) Creation of Genetic Map Datasheet Genotype data of possible NiF8-derived 3004 markers and Ni9-derived 4569 markers were obtained based on the signal data detected in 2 above of the NiF8 and Ni9 sugarcane varieties and the progeny line (line 191). Based on the obtained genotype data, chromosomal marker position information was obtained by calculation using the gene distance function (Kosambi) and the AntMap genetic map creation software (Iwata H, Ninomiya S (2006) AntMap: constructing genetic linkage maps using an ant colony optimization algorithm, Breed Sci 56: 371-378). Further, a genetic map datasheet was created based on the obtained marker position information using Mapmaker/EXP ver. 3.0 (A Whitehead Institute for Biomedical Research Technical Report, Third Edition, January, 1993).

(2) Acquisition of Stalk Sugar Content Data

Figure 3:
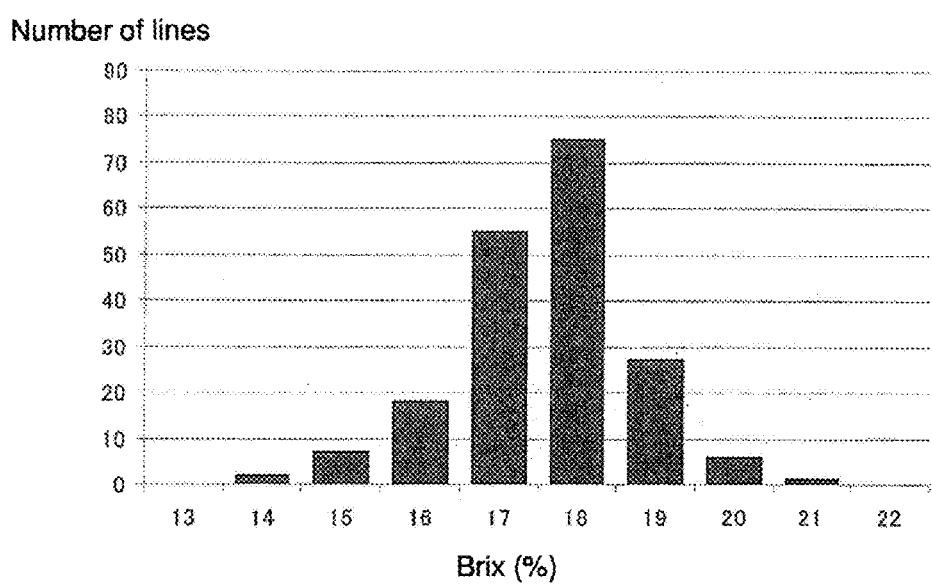
FIG. 3 is a characteristic chart showing stalk sugar content data for sugarcane variety/line groups used in the Examples.

The tested sugarcane varieties (NiF8 and Ni9) and the progeny line (line 191) were planted (13 individuals in each plot (2.2 m$^2$)) in April 2009. In March 2010, stalks of 5 individuals were harvested from each plot. The Brix value of the juice extracted from the harvested stalks was determined using a Brix meter. The mean Brix value was obtained for each line and the obtained mean values were used as stalk sugar content data. FIG. 3 is a chart summarizing the measured stalk sugar contents for the lines subjected to measurement. NiF8 and Ni9 are included in the "19 degrees Brix (%)" data zone and the "18 degrees Brix (%)" data zone, respectively.

(3) Quantitative Trait (Quantitative Trait Loci: QTL) Analysis

Figure 4:
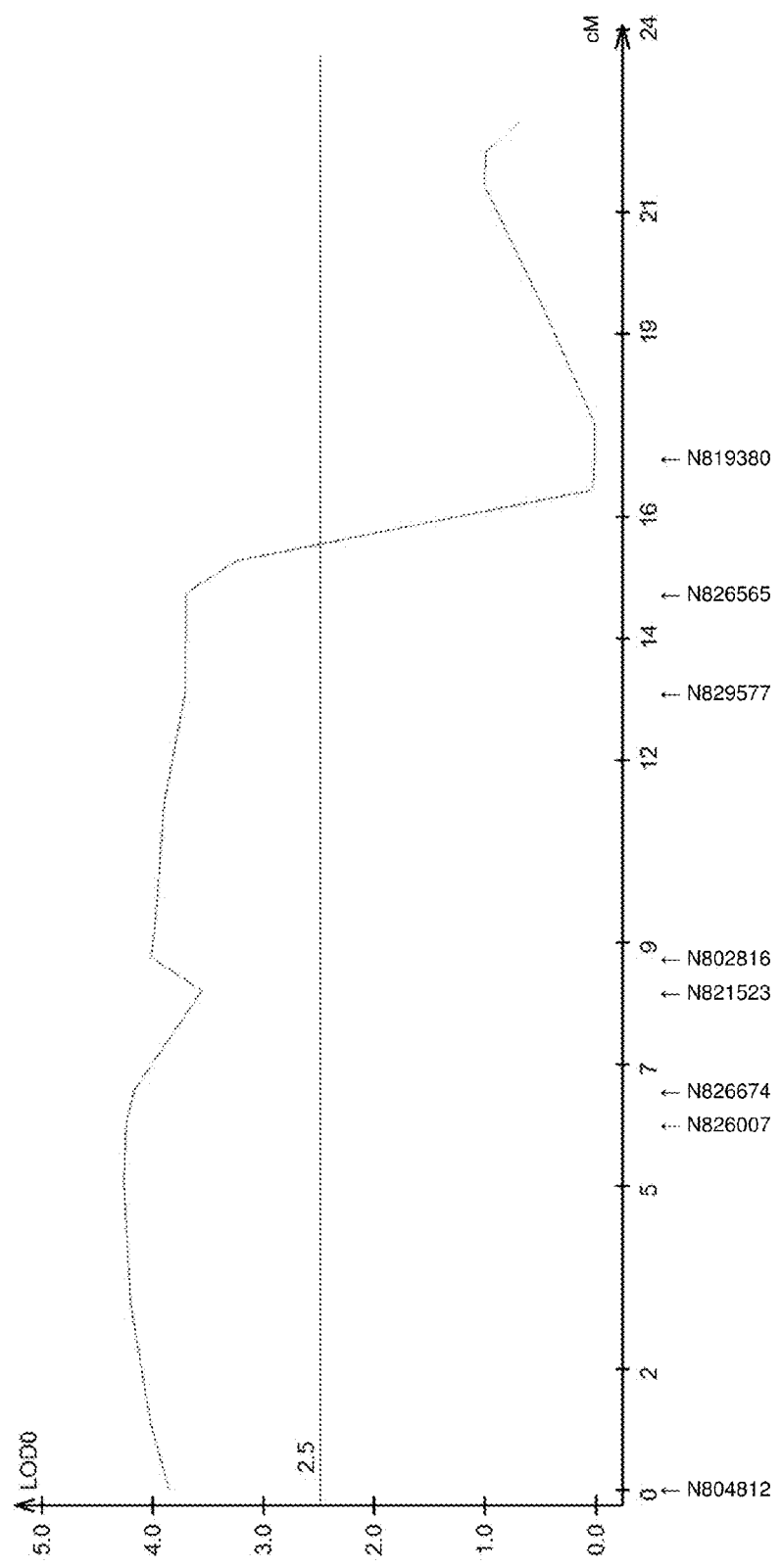
FIG. 4 is a characteristic chart showing QTL analysis results for the NiF8 sugarcane variety regarding stalk sugar content (the 53rd linkage group).
Figure 5:
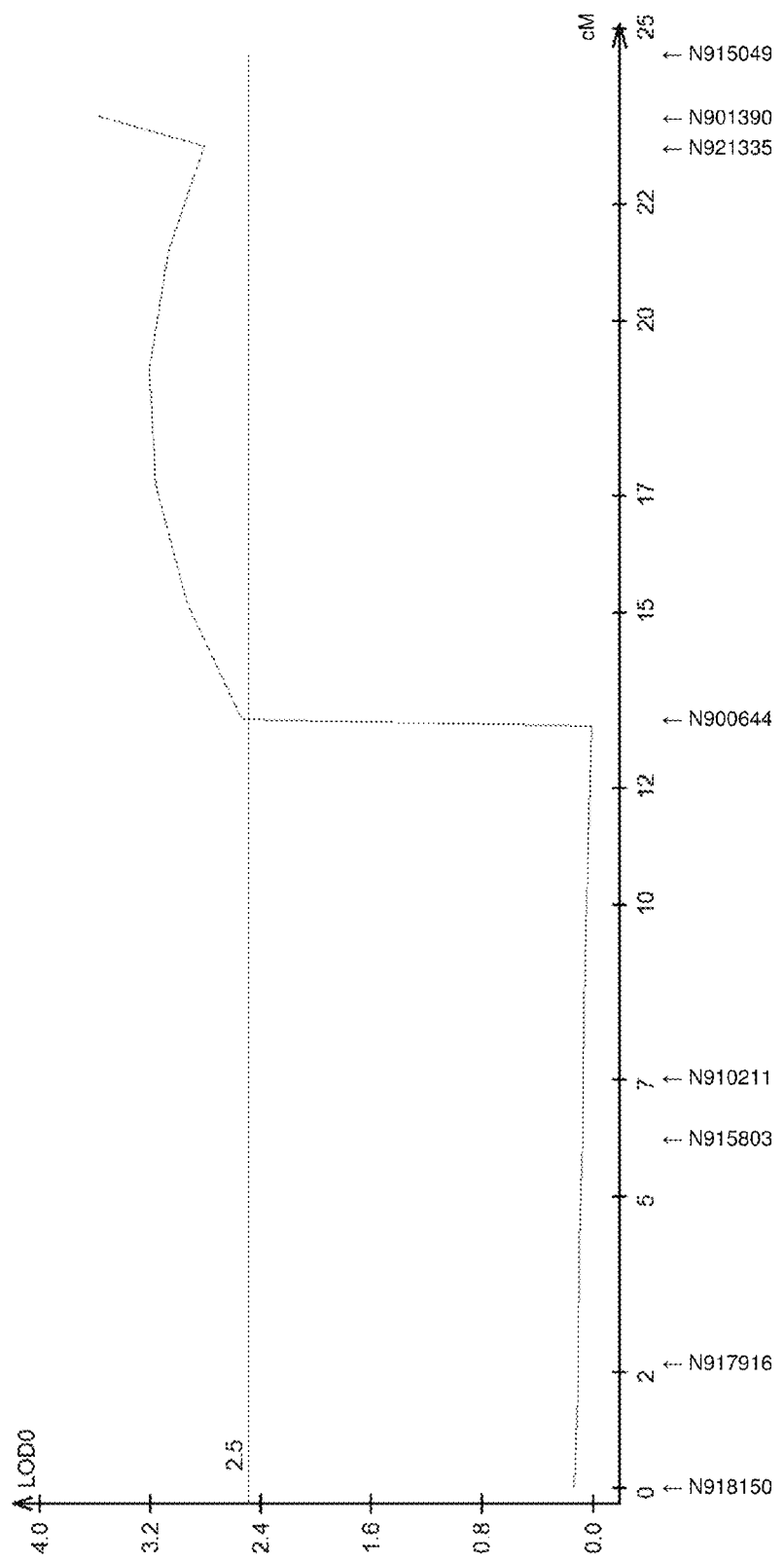
FIG. 5 is a characteristic chart showing QTL analysis results for the Ni9 sugarcane variety regarding stalk sugar content (the 61st linkage group).

Based on the genetic map datasheet obtained in (1) above and the stalk-sugar-content data obtained in (2) above, QTL analysis was carried out by the composite interval mapping (CIM) method using the QTL Cartographer gene analysis software (Wang S., C. J. Basten, and Z.-B. Zeng (2010). Windows QTL Cartographer 2.5. Department of Statistics, North Carolina State University, Raleigh, N.C.; http://statgen.ncsu.edu/qtlcart/cartographer.html). Upon analysis, the LOD threshold was determined to be 3.0. As a result, as shown in FIGS. 4 and 5, peaks exceeding the LOD threshold were observed in the following ranges: the range between markers N804812 and N819380 present in the 53rd linkage group of the NiF8 sugarcane variety; and the range between markers N918150 and N915049 present in the 61st linkage group of the Ni9 sugarcane variety. It was possible to specify the obtained peaks as shown in table 3, suggesting the presence of causative genes (i.e., gene group) each having the function of causing an increase in stalk sugar content at the peak positions.

Figure 6:
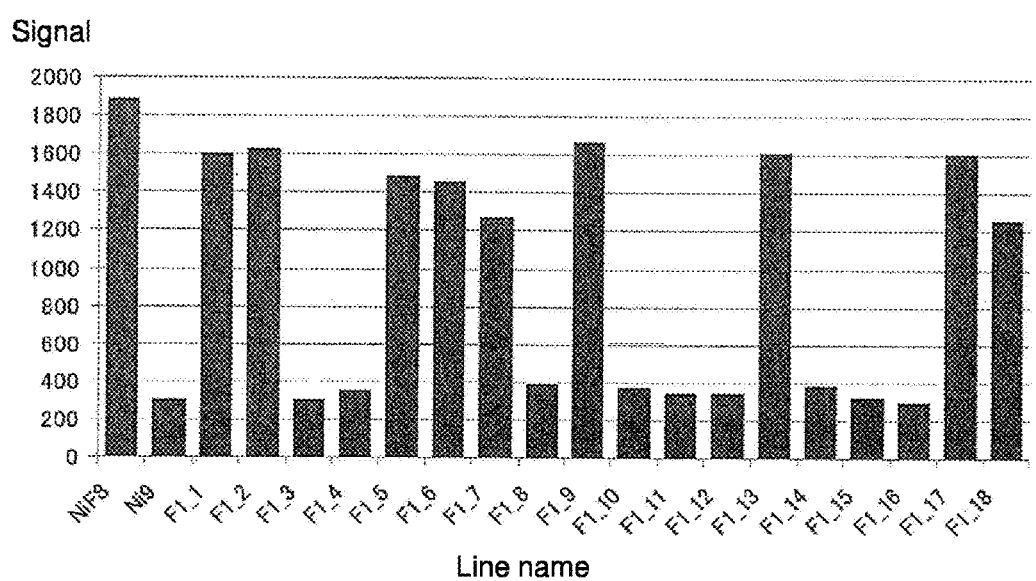
FIG. 6 is a characteristic chart showing signal levels of N821523 (a marker present in the 53rd linkage group of NiF8) for individual lines.
Figure 7:
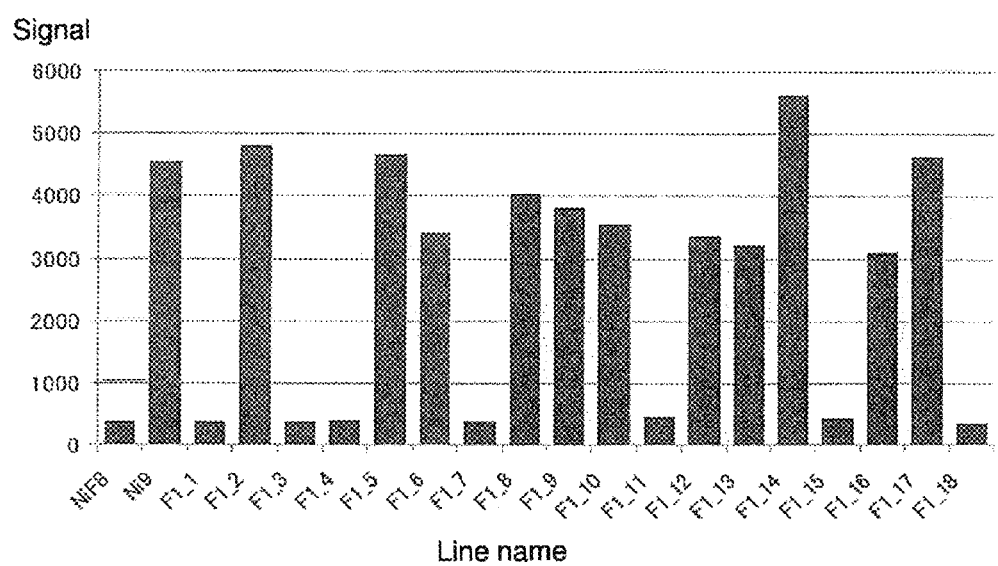
FIG. 7 is a characteristic chart showing signal levels of N917916 (a marker present in the 61st linkage group of Ni9) for individual lines.

As shown in FIGS. 4 and 5, markers located in the vicinity of the peaks are inherited in linkage with causative genes (i.e., gene group) each having the function of causing an increase in stalk sugar content. This shows that the markers can be used as sugarcane-stalk-sugar-content-related markers. Specifically, it has been revealed that the 16 types of markers shown in FIGS. 4 and 5 can be used as sugarcane-stalk-sugar-content-related markers. In addition, as examples of signals detected in 2 (6) above, table 4 shows signal levels of 16 types of markers among markers N804812 to N819380 present in the 53rd linkage group of the NiF8 sugarcane variety and markers N918150 to N915049 present in the 61st linkage group of the Ni9 sugarcane variety for NiF8 and Ni9 and their 18 progeny lines (F1_1 to F1_18). In particular, the signal levels of N821523 and N917916 are shown in FIGS. 6 and 7, respectively.

TABLE 3

| Linkage group | Position (cM) | Range (cM) | Adjacent marker | LOD value | Effect (%) |
|---|---|---|---|---|---|
| NiF8_53 | 5.1 | 17.5 | N804812-N819380 | 4.3 | 0.7 |
| Ni9_61 | 19.2 | 24.6 | N91815Q-N915049 | 3.2 | 0.6 |

TABLE 4

| Linkage group | Marker name | Line name | | | | | | | | | |
|---|---|---|---|---|---|---|---|---|---|---|---|
| | | NiF8 | Ni9 | F1_1 | F1_2 | F1_3 | F1_4 | F1_5 | F1_6 | F1_7 | F1_8 |
| NiF8_53 | N804812 | 3,181 | 530 | 3,946 | 3,962 | 740 | 598 | 4,847 | 3,195 | 3,184 | 481 |
| | N826007 | 1,834 | 413 | 1,241 | 1,254 | 410 | 454 | 1,307 | 1,158 | 1,253 | 477 |
| | N826674 | 8,061 | 459 | 5,736 | 5,260 | 591 | 436 | 5,418 | 4,477 | 3,876 | 438 |
| | N821523 | 1,890 | 308 | 1,599 | 1,631 | 307 | 349 | 1,486 | 1,457 | 1,268 | 391 |
| | N802816 | 2,035 | 675 | 1,190 | 1,400 | 936 | 426 | 1,930 | 1,506 | 1,866 | 402 |
| | N829577 | 2,690 | 635 | 2,468 | 2,000 | 846 | 473 | 2,089 | 2,034 | 2,034 | 614 |
| | N826565 | 4,086 | 761 | 5,484 | 4,323 | 773 | 700 | 6,299 | 3,779 | 2,863 | 713 |
| | N819380 | 2,295 | 567 | 2,076 | 1,477 | 423 | 384 | 1,156 | 1,387 | 1,037 | 384 |
| Ni9_61 | N918150 | 471 | 2,249 | 562 | 2,193 | 858 | 991 | 2,746 | 2,235 | 880 | 3,293 |
| | N917916 | 382 | 4,558 | 372 | 4,798 | 356 | 403 | 4,669 | 3,404 | 369 | 4,040 |
| | N915803 | 489 | 4,694 | 447 | 4,885 | 418 | 606 | 3,503 | 3,321 | 478 | 3,306 |
| | N910211 | 433 | 1,736 | 386 | 1,955 | 460 | 588 | 3,427 | 1,643 | 781 | 3,142 |
| | N900644 | 432 | 2,030 | 488 | 1,744 | 733 | 823 | 1,925 | 1,510 | 580 | 1,803 |
| | N921335 | 653 | 2,463 | 557 | 2,364 | 435 | 381 | 2,095 | 1,780 | 560 | 1,662 |
| | N901390 | 507 | 3,329 | 622 | 2,779 | 431 | 359 | 2,782 | 2,333 | 504 | 2,274 |
| | N915049 | 414 | 1,239 | 374 | 1,242 | 481 | 439 | 1,263 | 1,277 | 404 | 1,444 |

| Linkage group | Marker name | Line name | | | | | | | | | |
|---|---|---|---|---|---|---|---|---|---|---|---|
| | | F1_9 | F1_10 | F1_11 | F1_12 | F1_13 | F1_14 | F1_15 | F1_16 | F1_17 | F1_18 |
| NiF8_53 | N804812 | 3,998 | 426 | 668 | 430 | 3,398 | 505 | 507 | 456 | 3,566 | 3,925 |
| | N826007 | 1,162 | 404 | 400 | 461 | 1,316 | 419 | 571 | 400 | 1,228 | 1,097 |
| | N826674 | 3,988 | 594 | 458 | 407 | 5,868 | 422 | 394 | 438 | 6,037 | 5,690 |
| | N821523 | 1,669 | 367 | 342 | 341 | 1,608 | 375 | 326 | 292 | 1,607 | 1,262 |
| | N802816 | 2,211 | 617 | 634 | 715 | 1,480 | 407 | 362 | 410 | 1,562 | 2,241 |
| | N829577 | 2,351 | 551 | 501 | 878 | 2,005 | 384 | 574 | 436 | 2,341 | 1,898 |
| | N826565 | 4,080 | 563 | 537 | 658 | 3,596 | 800 | 586 | 647 | 4,187 | 3,089 |
| | N819380 | 1,654 | 368 | 374 | 472 | 1,899 | 438 | 402 | 472 | 1,668 | 1,443 |
| Ni9_61 | N918150 | 3,325 | 2,647 | 673 | 2,499 | 2,698 | 3,523 | 953 | 2,200 | 2,052 | 766 |
| | N917916 | 3,801 | 3,557 | 454 | 8,365 | 3,205 | 5,617 | 427 | 3,102 | 4,637 | 352 |
| | N915803 | 5,210 | 3,960 | 421 | 3,951 | 3,865 | 5,874 | 539 | 8,958 | 4,050 | 361 |
| | N910211 | 1,533 | 1,764 | 378 | 2,543 | 3,468 | 5,019 | 373 | 1,635 | 2,142 | 453 |
| | N900644 | 1,244 | 1,505 | 948 | 1,771 | 2,129 | 3,128 | 589 | 1,683 | 2,482 | 508 |
| | N921335 | 1,667 | 1,367 | 516 | 2,045 | 2,055 | 2,930 | 424 | 1,747 | 2,382 | 565 |
| | N901390 | 2,558 | 1,560 | 701 | 2,851 | 3,131 | 3,362 | 427 | 2,574 | 2,961 | 410 |
| | N915049 | 1,455 | 1,326 | 673 | 1,505 | 2,159 | 1,756 | 605 | 1,186 | 1,166 | 483 |

Signal levels of 16 types of markers were found to be very high for the progeny lines such as F1_2, F1_5, F1_6, F1_9, F1_13, and F1_17 with relatively high stalk sugar contents. These results also revealed that 16 types of markers among markers N804812 to N819380 present in the 53rd linkage group of the NiF8 sugarcane variety and markers N918150 to N915049 present in the 61st linkage group of the Ni9 sugarcane variety can be used as sugarcane-stalk-sugar-content-related markers.

All publications, patents, and patent applications cited herein are incorporated herein by reference in their entirety.

The invention claimed is:

1. A method for producing a sugarcane variety/line having an increased stalk sugar content, comprising:
   a step of extracting genomic DNA from a progeny plant, said progeny plant being a sugarcane variety/line or a hybrid line obtained from a cross of a sugarcane variety/line and a closely related variety/line; and
   a step of determining the presence of a sugarcane-stalk-sugar-content-related marker in the extracted genomic DNA, and selecting a sugarcane variety/line comprising the marker in its genome; thereby producing a sugarcane variety/line having an increased stalk sugar content, wherein the presence of the marker is determined by utilizing a DNA chip provided with probes, each probe corresponding to the sugarcane-stalk-sugar-content-related marker, and wherein said sugarcane-stalk-sugar-content-related marker comprises a full-length nucleotide sequence selected from the group consisting of the nucleotide sequences shown in SEQ ID NOS: 1 to 16.

2. The method for producing a sugarcane variety/line according to claim 1, wherein the progeny plant is in the form of seeds or a young seedling and the genomic DNA is extracted from the seeds or the young seedling.

* * * * *